(12) United States Patent
Broome et al.

(10) Patent No.: US 8,647,359 B2
(45) Date of Patent: Feb. 11, 2014

(54) DISTAL PROTECTION FILTER

(75) Inventors: Thomas E. Broome, Shakopee, MN (US); Verivada (Chandru) Chandrasekaran, Mercer Island, WA (US); John M. K. Daniel, Fremont, CA (US); James E. Mayberry, Champlin, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 383 days.

(21) Appl. No.: 10/044,368

(22) Filed: Jan. 10, 2002

(65) Prior Publication Data

US 2003/0130682 A1 Jul. 10, 2003

(51) Int. Cl.
*A61F 2/01* (2006.01)

(52) U.S. Cl.
USPC ........................................................ 606/200

(58) Field of Classification Search
USPC ................................. 606/200, 191
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,590,938 A | 5/1986 | Segura et al. | |
| 4,619,246 A | 10/1986 | Molgaard-Nielsen et al. | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,873,978 A | 10/1989 | Ginsburg | |
| 4,921,478 A | 5/1990 | Solano et al. | |
| 4,921,484 A | 5/1990 | Hillstead | |
| 4,926,858 A | 5/1990 | Gifford, III et al. | |
| 4,969,891 A | 11/1990 | Gewertz | |
| 4,998,539 A | 3/1991 | Delsanti | |
| 5,002,560 A | 3/1991 | Machold et al. | |

(Continued)

FOREIGN PATENT DOCUMENTS

| | | |
|---|---|---|
| DE | 28 21 048 | 7/1980 |
| DE | 34 17 738 | 11/1985 |

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

*Primary Examiner* — Darwin Erezo
(74) *Attorney, Agent, or Firm* — Seager, Tufte & Wickhem LLC

(57) ABSTRACT

Methods and devices for capturing debris within a blood vessel are disclosed. A filter assembly in accordance with the present invention comprises an elongate shaft having a proximal end and a distal end, and a filter fixed to the elongate shaft proximate the distal end thereof. A filter assembly in accordance with the present invention may further include a means for reducing the volume of the debris that is disposed within the filter.

34 Claims, 9 Drawing Sheets

(56) References Cited

U.S. PATENT DOCUMENTS

| | | | |
|---|---|---|---|
| 5,011,488 A | 4/1991 | Ginsburg | |
| 5,053,008 A | 10/1991 | Bajaj | |
| 5,071,407 A | 12/1991 | Termin et al. | |
| 5,100,423 A | 3/1992 | Fearnot | |
| 5,102,415 A | 4/1992 | Guenther et al. | |
| 5,133,733 A | 7/1992 | Rasmussen et al. | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,224,953 A | 7/1993 | Morgentaler | |
| 5,329,942 A | 7/1994 | Gunther et al. | |
| 5,330,484 A | 7/1994 | Gunther | |
| 5,354,310 A | 10/1994 | Garnie et al. | |
| 5,376,100 A | 12/1994 | Lefebvre | |
| 5,421,832 A | 6/1995 | Lefebvre | |
| 5,423,742 A | 6/1995 | Theron | |
| 5,449,372 A | 9/1995 | Schmaltz et al. | |
| 4,842,579 B1 | 10/1995 | Shiber | |
| 5,456,667 A | 10/1995 | Ham et al. | |
| 5,462,529 A | 10/1995 | Simpson et al. | |
| 5,536,242 A | 7/1996 | Willard et al. | |
| 5,549,626 A | 8/1996 | Miller et al. | |
| 5,658,296 A | 8/1997 | Bates et al. | |
| 5,662,671 A | 9/1997 | Barbut et al. | |
| 5,695,519 A | 12/1997 | Summers et al. | |
| 5,720,764 A | 2/1998 | Naderlinger | |
| 5,728,066 A | 3/1998 | Daneshvar | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,795,322 A | 8/1998 | Bouewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,846,260 A | 12/1998 | Maahs | |
| 5,848,964 A | 12/1998 | Samuels | |
| 5,876,367 A | 3/1999 | Kaganov et al. | |
| 5,895,399 A | 4/1999 | Barbut et al. | |
| 5,910,154 A | 6/1999 | Tsugita et al. | |
| 5,911,734 A | 6/1999 | Tsugita et al. | |
| 5,925,016 A | 7/1999 | Chornenky et al. | |
| 5,925,060 A | 7/1999 | Forber | |
| 5,925,062 A | 7/1999 | Purdy | |
| 5,935,139 A | 8/1999 | Bates | |
| 5,941,869 A | 8/1999 | Patterson et al. | |
| 5,941,896 A | 8/1999 | Kerr | |
| 5,947,995 A | 9/1999 | Samuels | |
| 5,954,745 A | 9/1999 | Gertler et al. | |
| 5,980,555 A | 11/1999 | Barbut et al. | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,814 A | 5/2000 | Ladd | |
| 6,066,149 A | 5/2000 | Samson et al. | |
| 6,066,158 A | 5/2000 | Engelson et al. | |
| 6,068,645 A | 5/2000 | Tu | |
| 6,086,605 A | 7/2000 | Barbut et al. | |
| 6,117,154 A | 9/2000 | Barbut et al. | |
| 6,129,739 A | 10/2000 | Khosravi | |
| 6,136,016 A | 10/2000 | Barbut et al. | |
| 6,142,987 A | 11/2000 | Tsugita | |
| 6,152,946 A | 11/2000 | Broome et al. | |
| 6,165,200 A | 12/2000 | Tsugita et al. | |
| 6,168,579 B1 | 1/2001 | Tsugita | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 * | 6/2001 | Daniel et al. | 606/200 |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 | 2/2002 | Levinson et al. | |
| 6,436,120 B1 * | 8/2002 | Meglin | 606/200 |
| 6,565,591 B2 * | 5/2003 | Brady et al. | 606/200 |
| 6,605,102 B1 * | 8/2003 | Mazzocchi et al. | 606/200 |
| 6,652,554 B1 * | 11/2003 | Wholey et al. | 606/200 |
| 6,663,652 B2 * | 12/2003 | Daniel et al. | 606/200 |
| 6,682,546 B2 * | 1/2004 | Amplatz | 606/200 |
| 6,793,666 B2 * | 9/2004 | Hansen et al. | 606/200 |
| 6,840,950 B2 * | 1/2005 | Stanford et al. | 606/200 |
| 6,939,361 B1 * | 9/2005 | Kleshinski | 606/200 |
| 6,989,019 B2 * | 1/2006 | Mazzocchi et al. | 606/200 |
| 7,001,407 B2 * | 2/2006 | Hansen et al. | 606/200 |
| 7,033,375 B2 * | 4/2006 | Mazzocchi et al. | 606/200 |
| 2001/0012951 A1 | 8/2001 | Bates et al. | |
| 2002/0045916 A1 * | 4/2002 | Gray et al. | 606/200 |
| 2002/0095172 A1 * | 7/2002 | Mazzocchi et al. | 606/200 |

FOREIGN PATENT DOCUMENTS

| | | |
|---|---|---|
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |

(56) References Cited

FOREIGN PATENT DOCUMENTS

| | | |
|---|---|---|
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01//67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |
| WO | WO 01/97714 A1 | 12/2001 |

OTHER PUBLICATIONS

"Endovascular Grafts, Stents Drive Interventional Radiology Growth," *Cardiovascular* Device Update, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneoin Vena Cava Filger," *AJR*, 141:601-604.

Cragg, Andrew et al., "Nonsurgical Placement of Arterial Endoprosthesis: A New Technique Using Nitinol Wire," AJR, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," Surgery, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," Cardiovascular Surgery, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," Catheterization and Cardiovascular Diagnosis, 31:17-84 (1994).

Moussa, MD, Issaam "Stents Don't Require Systemic.Anticoagulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiolgy, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al.; "Distal Embolization is Common After Directional Atherectomy . . . ," American Heart Journal, 129(3):430-435 (1995).

Wholey, Mark H. et al., PTA and Stents in the Treatment of Extracranial Circulation, *The Journal of Invasive Cardiology*, 8(E):25E-30E (1996).

\* cited by examiner

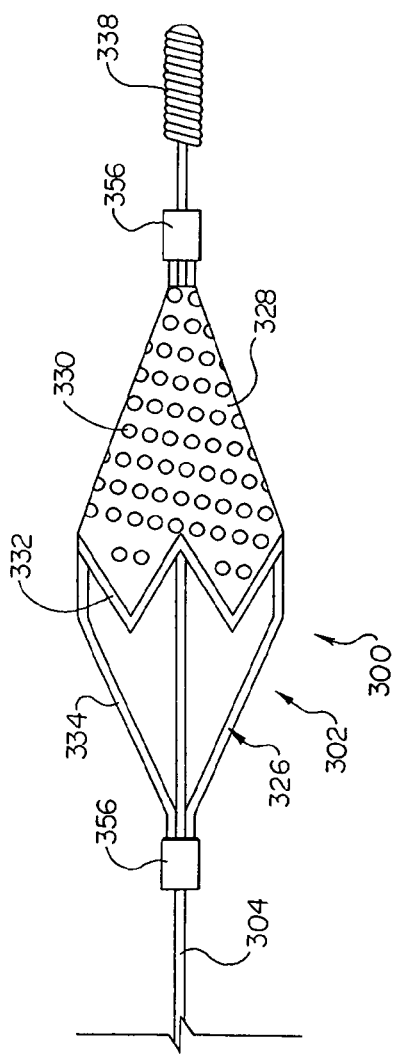

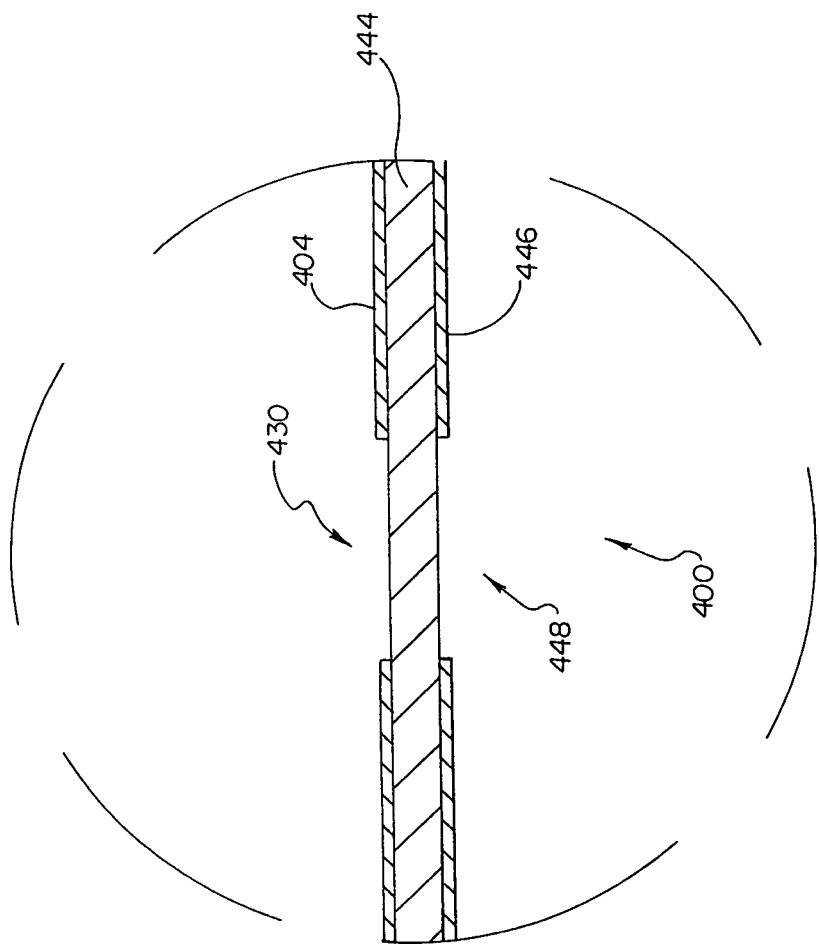

DISTAL PROTECTION FILTER

FIELD OF THE INVENTION

The present invention relates generally to devices and methods for treating occluded or stenoic blood vessels. More particularly, the present invention relates to devices and methods for providing temporary placement of a filter in a blood vessel during a procedure to remove an occlusion or stenosis.

BACKGROUND OF THE INVENTION

It is critical to the health of the human body that the heart muscle be well oxygenated so that the blood pumping action of the heart is not impaired. Blood vessels which have become occluded (blocked) or stenotic (narrowed) may interrupt the oxygen supply to the heart muscle.

Occluded or stenotic blood vessels may be treated with a number of medical procedures including angioplasty and atherectomy. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. During an atherectomy procedure, the stenotic lesion is mechanically cut or abraded away from the blood vessel wall using an atherectomy catheter.

During atherectomy procedures, stenotic debris that is separated from the stenosis may be free to flow within the lumen of the vessel. If this debris enters the circulatory system, it may facilitate the formation of an occlusion in the neural vasculature or in the lungs, both of which are highly undesirable. An occlusion in the neural vasculature may cause a stroke, and an occlusion in the lungs may interfere with the oxygenation of the blood. During angioplasty procedures, stenotic debris may also break loose due to manipulation of the blood vessel.

Stenotic debris may be captured by placing a filter distally of the site where atherectomy, angioplasty, etc. is being performed. Stenotic debris flowing within the vessel may be captured within the filter. As the volume of the captured debris increases, it may become necessary to remove the filter from the body so that the captured debris can be removed therefrom. Repeatedly removing the filter from the body for emptying may extend the length of the procedure and increase the wear and tear on the patient's vasculature.

SUMMARY OF THE INVENTION

The present invention relates generally to devices and methods for treating occluded or stenoic blood vessels. More particularly, the present invention relates to devices and methods for providing temporary placement of a filter in a blood vessel during a procedure to remove an occlusion or stenosis. In an implementation of the present invention the filter includes a first portion and a second portion. The first portion preferably has a generally conical shape defining a base diameter, an apex, and a first included angle. The second portion preferably has a shape that may be generally described as a truncated cone. The second portion defines a second included angle, a first diameter and a second diameter.

In another embodiment in accordance with the present invention comprises an elongate shaft having a proximal end and a distal end, and a filter fixed to the elongate shaft proximate the distal end thereof. A filter assembly in accordance with the present invention may further include a means for reducing the volume of the debris that is disposed within the filter. In certain implementations of the invention, the means for reducing the volume of the captured debris comprises a lumen defined by the elongate shaft. A fluid source may be coupled to the proximal end of the elongate shaft such that it fluidly communicates with the lumen. A pharmaceutical agent may be injected into the lumen and delivered to a location proximate the filter. In one aspect of the present invention, the pharmaceutical agent is one that will partially or completely dissolve the captured debris.

In another implementation of the present invention, the elongate shaft comprises an electrically conductive core and an electrically insulating layer overlaying the electrically conductive core. In this implementation of the invention, the means for reducing the volume of the captured debris may comprise a radio frequency energy source electrically coupled to the conductive core of the elongate shaft and at least one aperture extending through the electrically insulating layer of the elongate shaft. In one aspect of the present invention, radio frequency energy may be used to ablate the captured debris.

BRIEF DESCRIPTION OF THE DRAWINGS

FIG. 7 is a plan view of a filter assembly that may be used in conjunction with the filter system of FIG. 6;

FIG. 8 is an additional plan view of the filter assembly of FIG. 7;

FIG. 10 is an enlarged cross-sectional view an electrode for use in a filter assembly in accordance with an additional exemplary embodiment of the present invention.

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives that may be utilized.

Figure 1:
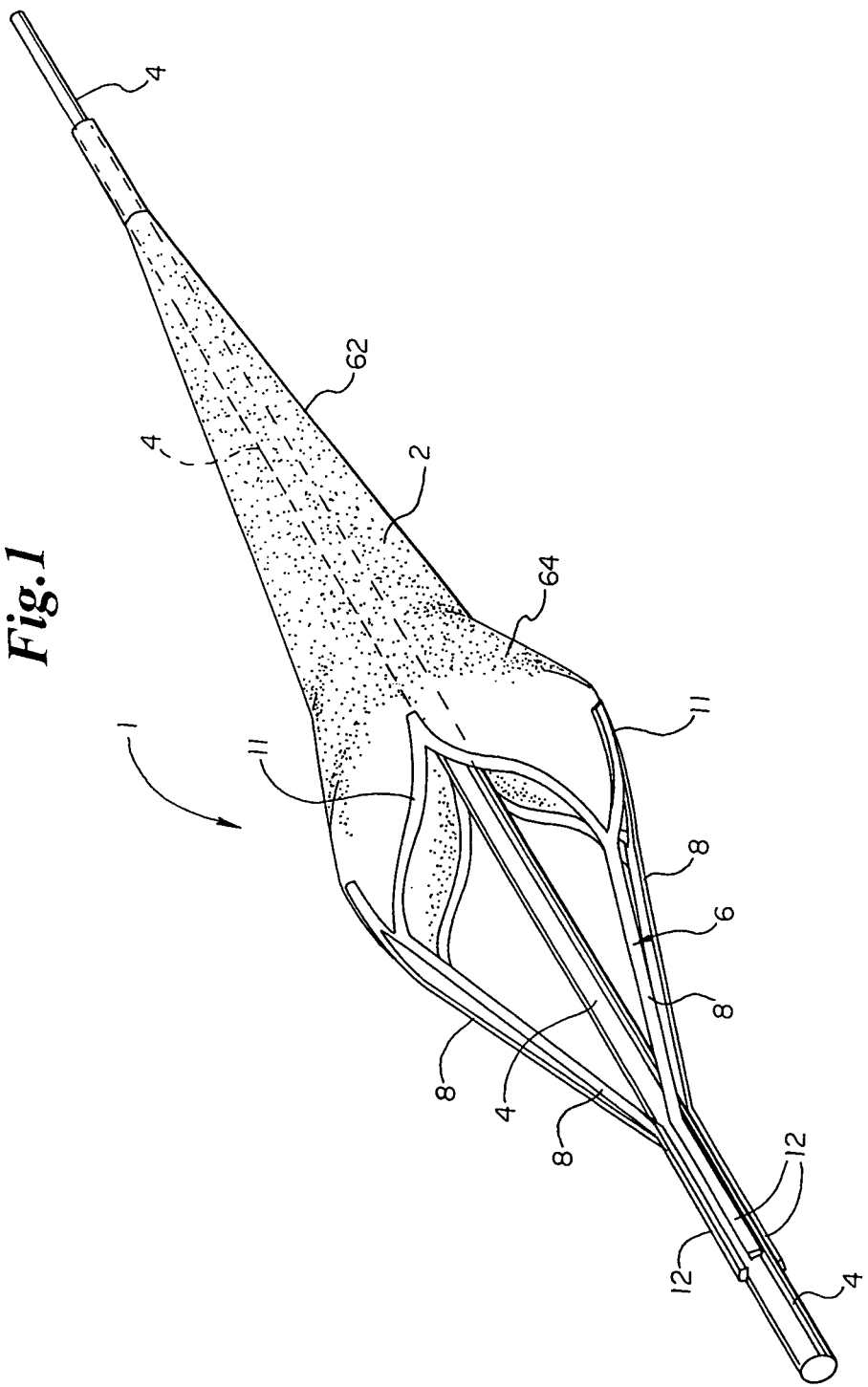
FIG. 1 is a perspective view of a filter assembly in accordance with the present invention.

FIG. 1 is a perspective view of a filter assembly 1 in accordance with the present invention. Filter assembly 1 includes a filter or filter fabric 2 connected to an elongate shaft 4. Proximal end of filter 2 defines a filter mouth. The filter mouth can be biased into an open position by a strut assembly 6 including a plurality of struts 8. Struts 8 are connected at their proximal ends to a filter mouth frame 11, and at their distal ends to strut attachment legs 12. Attachment legs 12 are preferably connected to shaft 4 by solder brazing or adhesive. Filter 2 can include a first portion 62 and a second portion 64. Second portion 64 can have a wall to shaft angle greater than the wall to shaft angle of first portion 62. The significance of this feature will be explained in more detail below.

Figure 2:
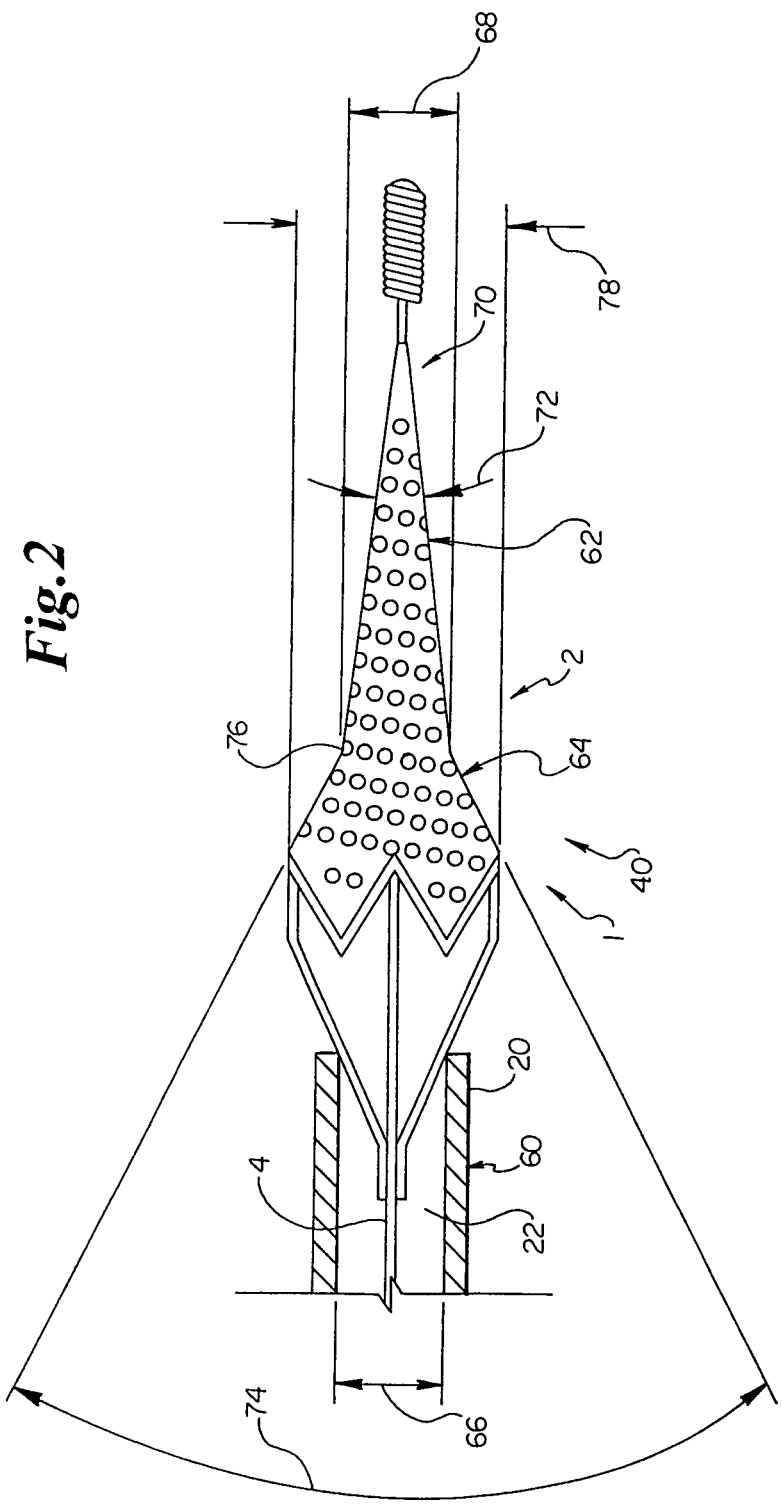
FIG. 2 is a plan view of the filter system including the filter assembly of FIG. 1.

FIG. 2 is a plan view of filtering system 40 in accordance with an additional embodiment of the present invention. Filtering system 40 of FIG. 2 includes filter assembly 1 of FIG. 1 and a retrieval sheath 60. Retrieval sheath 60 includes a wall 20 defining a lumen 22 having an inner diameter 66. Filter assembly 1 comprises an elongate shaft 4 and a filter 2. In a preferred embodiment, filter 2 may be urged to a position within lumen 22 of retrieval sheath 60, for example, by pulling on a proximal end of elongate shaft 4.

In the embodiment of FIG. 2, filter 2 is shown having an expanded shape. In a preferred embodiment, filter 2 has an expanded shape and a contracted shape. Filter 2 may assume the contracted shape when it is urged into lumen 22 of retrieval sheath 60.

In the embodiment of FIG. 2, first portion 62 has a generally conical shape defining a base diameter 68, an apex 70, and a first included angle 72. Also in the embodiment of FIG. 2, second portion 64 has a shape which may be generally described as a truncated cone. Second portion 64 of FIG. 2 defines a second included angle 74, a first diameter 76 and a second diameter 78.

In a preferred embodiment, base diameter 68 of first portion 62 is similar to inner diameter 66 of retrieval sheath 60 when filter 2 assumes an expanded shape. In a particularly preferred embodiment, first portion 62 is configured so that it is capable of assuming a base diameter that is generally smaller than inner diameter 66 of retrieval sheath 60 when filter 2 assumes a contracted shape. In this particularly preferred embodiment, the expansion of first portion 62 is limited so that base diameter 68 of first portion 62 is generally less than or equal to inner diameter 66 of retrieval sheath 60 when filter 2 assumes an expanded shape. Limiting the expansion of base diameter 68 of first portion 62 preferably reduces the likelihood that debris captured by filter 2 will cause first portion 62 to excessively bulge radially outward as filter 2 is urged into lumen 22 of retrieval sheath 60. Limiting the expansion of base diameter 68 of first portion 62 also preferably reduces the likelihood that a physician will be unable to pull filter 2 within lumen 22 of retrieval sheath 60.

In a preferred embodiment, second diameter 78 of second portion 64 is similar to the diameter of a blood vessel when filter 2 assumes an expanded shape. Also in a preferred embodiment, first diameter 76 of second portion 64 is similar to base diameter 68 of first portion 62. In a particularly preferred embodiment, first diameter 76 of second portion 64 is substantially equal to base diameter 68 of first portion 62.

In a preferred embodiment of filter 2, first included angle 72 of first portion 62 is, for example, between about 3 degrees and about 30 degrees when filter 2 assumes an expanded shape. In a particularly preferred embodiment of filter 2, first included angle 72 of first portion 62 is, for example, between about 7 degrees and about 55 degrees when filter 2 assumes an expanded shape.

In a preferred embodiment of filter 2, second included angle 74 of second portion 64 is, for example, between about 35 degrees and about 90 degrees when filter 2 assumes an expanded shape. In a particularly preferred embodiment of filter 2, second included angle 74 of second portion 64 is, for example, between about 40 degrees and about 60 degrees when filter 2 assumes an expanded shape.

Figure 3:
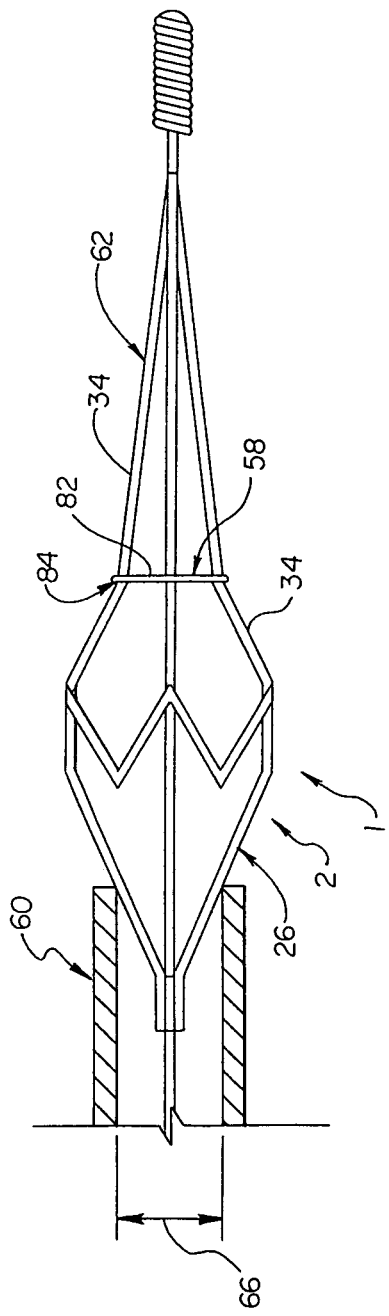
FIG. 3 is an additional plan view of the filter system of FIG. 2.

FIG. 3 is an additional plan view of filter assembly 1 of FIG. 2. In FIG. 3, filter 2 is shown without membrane 28. In FIG. 3, it may be appreciated that filter assembly 1 includes a frame 26 comprising a plurality of struts 34. In the embodiment of FIG. 3, frame 26 also includes a limiter 58 that is coupled to struts 34.

In a preferred embodiment, limiter 58 limits the expansion of first portion 62 of filter 2 so that base diameter 68 is similar to inner diameter 66 of retrieval sheath 60 when filter 2 assumes the expanded shape. In the embodiment of FIG. 3, limiter 58 comprises a wire 82 which forms a loop 84 disposed about struts 34. Limiter 58 may comprise various limiting elements without deviating from the spirit and scope of the present invention. Examples of limiting elements that may be suitable in some applications include wires, threads, rings, hooks, and loops.

Figure 4:
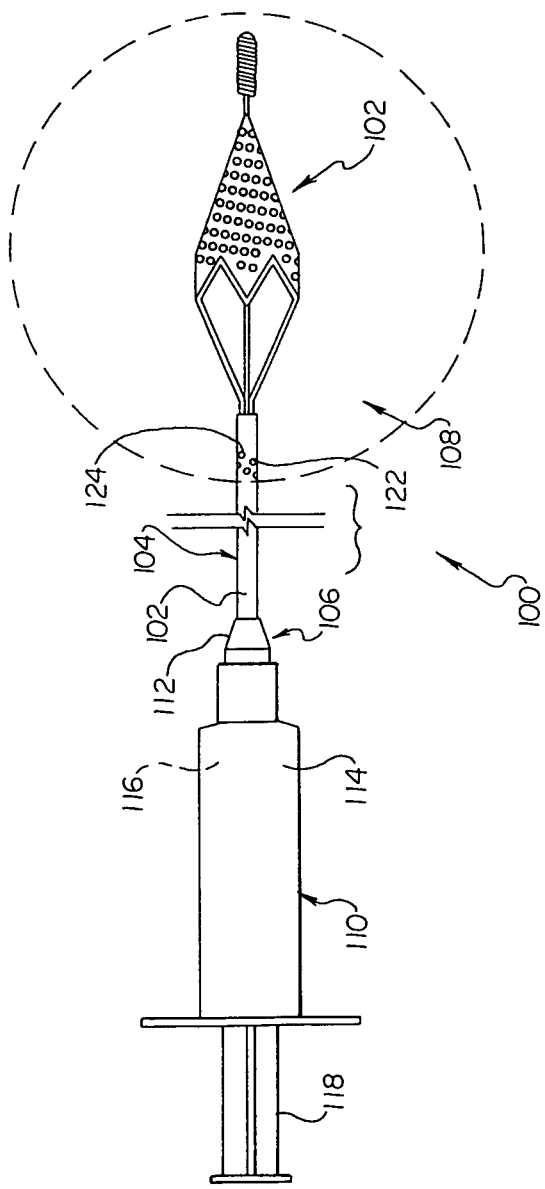
FIG. 4 is a plan view of a filter assembly in accordance with an additional embodiment of the present invention.

FIG. 4 is a plan view of a filter assembly 100 in accordance with an exemplary embodiment of the present invention. Filter assembly 100 includes an elongate shaft 104 having a proximal end 106, a distal end 108, and a filter 102 that is preferably fixed to elongate shaft 104 proximate distal end 108 thereof. Elongate shaft 104 of filter assembly 100 includes a wall 120 defining a lumen 122 and a plurality of apertures 124. In the embodiment of FIG. 1, apertures 124 are disposed proximate filter 102.

In FIG. 4, a fluid source 110 of filter assembly 100 is shown coupled to a hub 112 that is disposed about elongate shaft 104 proximate proximal end 106 thereof. Fluid source 110 is preferably capable of injecting fluid into lumen 122 of elongate shaft 104. In the embodiment of FIG. 4, fluid source 110 includes a housing 114 defining a variable volume chamber 116 that is preferably in fluid communication with lumen 122 of elongate shaft 104. In this exemplary embodiment, fluid source 110 further includes a plunger 118 slidingly disposed within variable volume chamber 116. Urging plunger 118 distally preferably urges fluid from variable volume chamber 116 through lumen 122 and out of apertures 124.

In a preferred embodiment, apertures 124 are disposed proximate filter 102. In a preferred method in accordance with the present invention, a pharmaceutical agent may be injected into lumen 122 and delivered to a location proximate filter 102. The pharmaceutical agent is preferably one that will partially or completely dissolve debris that is captured within filter 102.

Various energy sources may be utilized to urge plunger 118 distally. Energy sources that may be suitable in some applications include springs, compressed gas, a human being, and electricity. It will be appreciated that many embodiments of fluid source 110 are possible without deviating from the spirit and scope of the present invention. Examples of fluid sources that may be suitable in some applications include peristaltic pumps, I.V. pumps, and I.V. bags.

Figure 5:
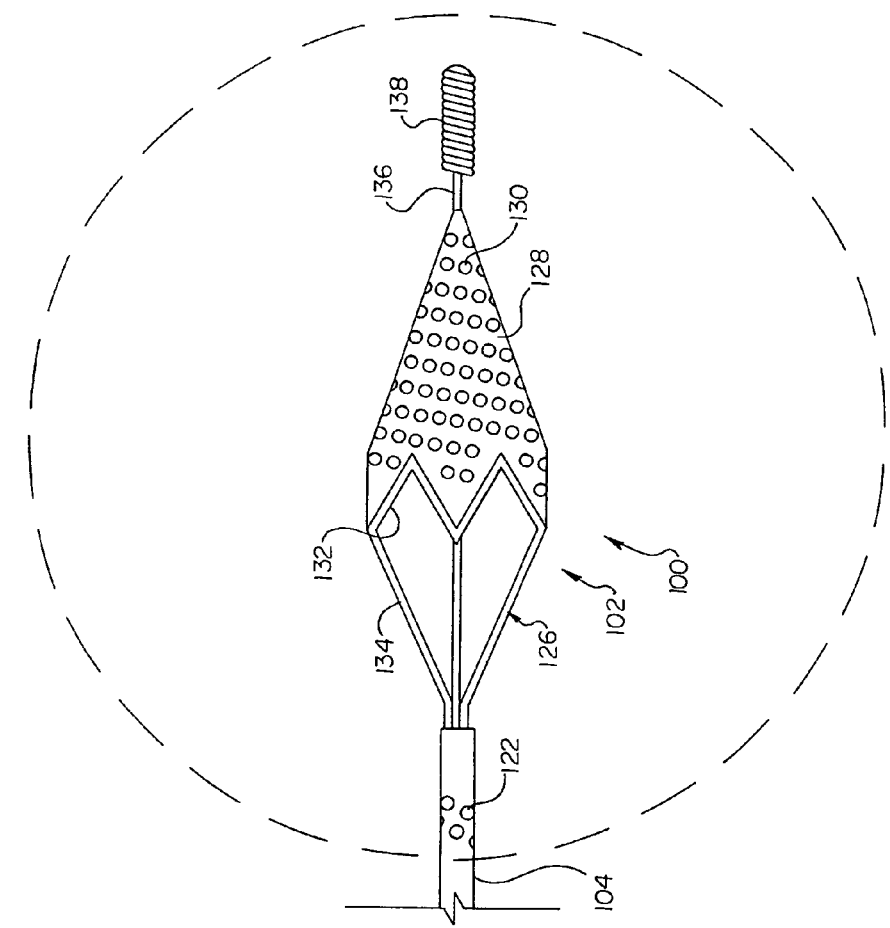
FIG. 5 is an enlarged plan view of a portion of the filter assembly of FIG. 4.

FIG. 5 is an enlarged plan view of a portion of filter assembly 100 of FIG. 4. In FIG. 5 it may be appreciated that filter 102 includes a frame 126 and a membrane 128 disposed in a generally conical arrangement. Membrane 128 defines a plurality of holes 130 extending therethrough. In the embodiment of FIG. 4, frame 126 includes zigzag member 132 and a plurality of struts 134. Zigzag member 132 is preferably configured such that it has a contracted shape and an expanded shape. In a preferred embodiment, the contracted shape and the expanded shape of zigzag member 132 are both generally cylindrical. In a particularly preferred embodiment, the contracted shape has a contracted radius that is smaller than an expanded radius of the expanded shape of zigzag member 132. Filter membrane 128 may be adhered to zigzag member 132, for example, by a solvent casting method, wherein the liquid membrane polymer is dipped over the zigzag member 132 and allowed to cure and solidify.

In the embodiment of FIG. 5, a portion of each strut 134 is disposed within lumen 122 of elongate shaft 104. Struts 134 are preferably fixed to elongate shaft 104. Various fixing methods may be used to fix struts 134 to elongate shaft 104 without deviating from the spirit and scope of the present invention. Examples of methods that may be suitable in some applications include soldering, brazing, adhesive bonding, mechanical coupling, and welding. Examples of welding processes that may be suitable in some applications include LASER welding, resistance welding, TIG welding, and microplasma welding. LASER welding equipment that may be suitable in some applications is commercially available from Unitek Miyachi of Monrovia, Calif. and Rofin-Sinar Incorporated of Plymouth, Mich. Resistance welding equipment that may be suitable in some applications is commercially available from Palomar Products Incorporated of Carlsbad, Calif. and Polaris Electronics of Olathe, Kans. TIG welding equipment that may be suitable in some applications is commercially available from Weldlogic Incorporated of Newbury Park, Calif. Microplasma welding equipment that may be suitable in some applications is commercially available from Process Welding Systems Incorporated of Smyrna, Tenn.

At the distal end of filter 102, membrane 128 may be adhered to a spine 136 of filter 102 by a suitable adhesive such as, for example, cyanoacrylates. In the embodiment of FIG. 2, a coil tip 138 is disposed at the distal end of spine 136.

Membrane 128 of filter 102 preferably has a thickness of between 25 microns and 100 microns and most preferably about 40 microns. Membrane 128 is preferably formed from polyurethane or other biocompatible material such as, for example, polyesters or silicones. Filter 102 can be coated with various coatings to impart various functional performance characteristics, one example being a thrombus resistant coating such as Heparin to discourage clot formation on filter 102. Holes 130 can be formed using various methods. Examples of processes that may be suitable in some applications include LASER cutting, punching, and drilling. LASER cutting equipment that may be suitable in some applications is commercially available from Unitek Miyachi of Monrovia, Calif. and Rofin-Sinar Incorporated of Plymouth, Mich. Drills and punches that may be suitable in some applications are commercially available from Technical Innovations Incorporated of Brazoria Tex. A micro drill press is commercially available from Louis Levin & Sons Incorporated of LaMirada, Calif. which identifies it with the model number 0021-07. An additional micro drill press is commercially available from National Jet Drill Company of Cumberland, Md. which identifies it as a NAJET model 1M. Yet another micro drill press is commercially available from Minitool Incorporated of Cambell, Calif. which identifies it as an ULTRA DRILL 4000.

The size of holes 130 can vary along the length of filter 102 for example, larger holes may be placed more proximally and smaller holes more distally or vice versa. The size of the holes may transition gradually or abruptly in a proximal or distal direction. The holes shape can vary from circular a shape to rectangular, square, trapezoidal, oval, slit or other shape. A circular aperture may have a diameter of, for example, 100 microns whereas a slit may have a width of 100 microns and a length of 100 microns. The edges of the holes can be mechanically or chemically chamfered, etched or polished to provide a smooth and rounded layer to streamline the passage of blood from within the conical shape portion of the filter to outside of the filter. To limit thrombus formation, the holes size and design may be such that the shear forces that blood components are exposed to are appropriate while blood is passing through the filter. Thus, aperture sizes may be selected to limit stagnation and re-circulation of blood in and around the filter while the filter is in use.

Elongate shaft 104 is preferably configured such that it may be used as a guidewire for advancing surgical instruments thereover. For example, an angioplasty balloon could be advanced over elongate shaft 104 to a location just proximal of filter 102. While filter 102 is deployed, angioplasty can be performed. Plaque and thrombus dislodged by the procedure will then drift distally into filter 102. Other procedures may be performed in this way including, for example, atherectomy and stent placement.

Embodiments of the filter 102 are possible in which frame 126 comprises a shape memory material. Examples of shape memory materials that may be suitable in some applications include shape memory alloys and shape memory polymers. Examples of shape memory alloys that may be suitable in some applications include Nitinol. The word Nitinol was coined by a group of researchers at the United States Naval Ordinance Laboratory (NOL) who were the first to observe the shape memory behavior of this material. The word Nitinol is an acronym including the chemical symbol for nickel (Ni), the chemical symbol for titanium (Ti), and the acronym for identifying the Naval Ordinance Laboratory (NOL). Nitinol is commercially available from Memry Technologies (Brookfield, Conn.), TiNi Alloy Company (San Leandro, Calif.), and Shape Memory Applications (Sunnyvale, Calif.).

Figure 6:
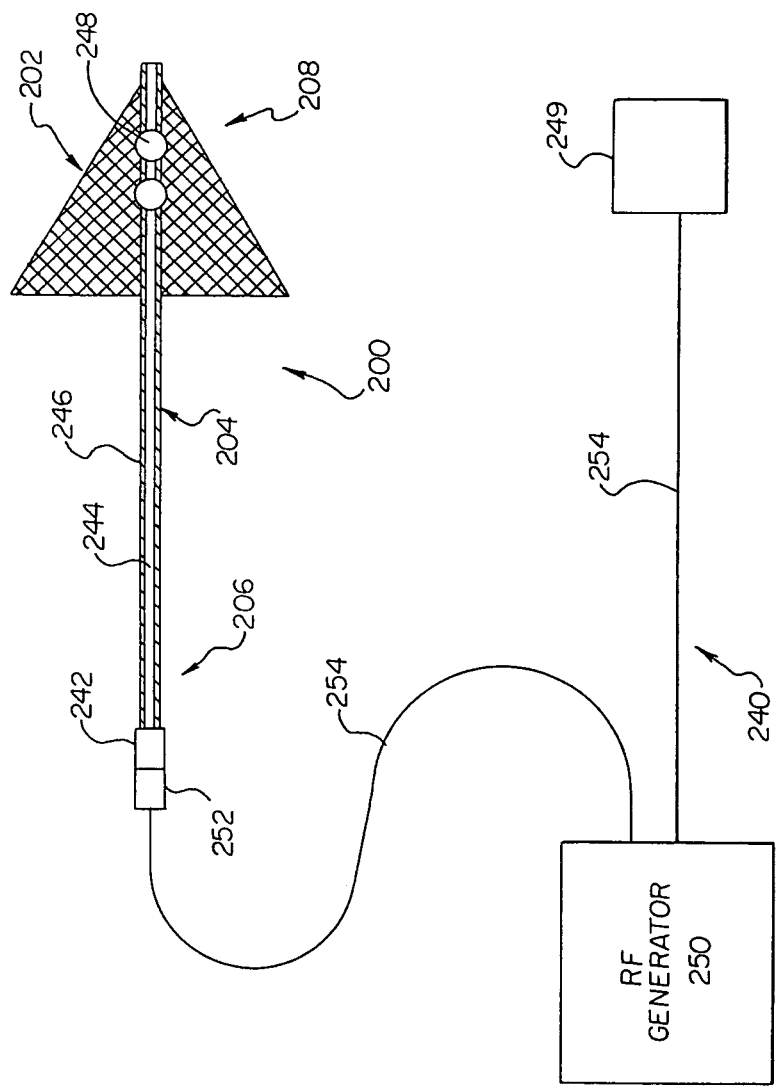
FIG. 6 is a diagrammatic representation of a filtering system in accordance with an additional exemplary embodiment of the present invention.

FIG. 6 is a diagrammatic representation of a filtering system 240 in accordance with an additional exemplary embodiment of the present invention. Filtering system 240 comprises a filter assembly 200 including an elongate shaft 204 having a proximal end 206 and a distal end 208. A filter 202 is preferably fixed to elongate shaft 204 proximate distal end 208 thereof. In the embodiment of FIG. 6, an electrical connector 242 is disposed at proximal end 206 of elongate shaft 204.

Elongate shaft 204 of FIG. 6 comprises an electrically conductive core 244 and an electrically insulating layer 246 overlaying electrically conductive core 244. In the embodiment of FIG. 6, a plurality of electrodes 248 are disposed proximate filter 202. Electrodes 248 are preferably coupled to electrically conductive core 244 of elongate shaft 204. In a preferred method in accordance with the present invention, electrodes 248 may be used to ablate debris captured by filter 202.

In FIG. 6, an RF generator 250 is shown coupled to electrically conductive core 244 of elongate shaft 204 via electrical connector 242, a mating connector 252 and a first lead wire 254. Filtering system 240 also includes a return electrode 249 coupled to RF generator 250 by a second lead wire 254. Return electrode 249 is preferably adapted for connection to the body of a patient. Return electrode 249 in the embodiment of FIG. 6 is pictured as a flat pad. Return electrode 249 may comprise, for example, a flexible conductive pad that conforms to the contours of a patient's body. Materials suitable for the conductive pad include metal foil and conductive ink disposed on a polymer substrate. Return electrode 249 is preferably adhered to the outside of a patient's body with an interface material that is both conductive and sticky, such as a hyrodgel adhesive. This configuration of an electrode disposed on a elongate shaft, and passive electrode pad may be referred to as a monopolar configuration. Bipolar embodiments of the present invention are also possible. In a bi-polar configuration, a return, or neutral electrode is disposed in close proximity to the electrode. For example, a return electrode could be disposed on an outer surface of insulating layer 246 of elongate shaft 204.

FIG. 7 is a plan view of a filter assembly 300 that may be used in conjunction with the filtering system of FIG. 6. In FIG. 7 it may be appreciated that filter assembly 300 includes a filter 302 comprising a frame 326 and a membrane 328 disposed in a generally conical arrangement. Membrane 328 defines a plurality of openings 330 extending therethrough. In the embodiment of FIG. 6, frame 326 includes zigzag member 332 and a plurality of struts 334. Zigzag member 332 is preferably configured such that it has a contracted shape and an expanded shape. In a preferred embodiment, the contracted shape and the expanded shape of zigzag member 332 are both generally cylindrical. In a particularly preferred embodiment, the contracted shape has a contracted radius that is smaller than an expanded radius of the expanded shape of zigzag member 332. Filter membrane 328 may be adhered to zigzag member 332, for example, by a solvent casting method, wherein the liquid membrane polymer is dipped over the zigzag frame and allowed to cure and solidify.

Frame 326 also includes a plurality of struts 334. In the embodiment of FIG. 7, a proximal portion of each strut 334 is fixed to elongate shaft 304 using a proximal collar 356. In the embodiment of FIG. 7, a distal portion of each strut 334 is fixed to elongate shaft 304 using a distal collar 356. It is to be appreciated that various fixing methods may be used to fix struts 334 to elongate shaft 304 without deviating from the spirit and scope of the present invention. Examples of methods that may be suitable in some applications include soldering, brazing, adhesive bonding, mechanical coupling, and welding. At the distal end of filter 302, membrane 328 may be adhered to a struts 334 of filter 302 with a suitable adhesive such as, for example, cyanoacrylates. In the embodiment of FIG. 7, a coil tip 338 is disposed at the distal end of elongate shaft 304.

Elongate shaft 304 is preferably configured such that it may be used as a guidewire for advancing surgical instruments thereover. For example, an angioplasty balloon could be advanced over elongate shaft 304 to a location just proximal of filter 302. While filter 302 is deployed, an angioplasty procedure can be performed. Plaque and thrombus dislodged by the procedure will then drift distally into filter 302. Other procedures may be performed in this way including, for example, atherectomy and stent placement.

FIG. 8 is an additional plan view of filter assembly 300 of FIG. 7. In FIG. 8, filter 302 is shown without membrane 328. In FIG. 8, it may be appreciated that filter assembly 300 includes a plurality of electrodes 348. Electrodes 348 are preferably located proximate frame 326 of filter 302. In a preferred embodiment, electrodes 348 may be utilized to ablate debris that is disposed within filter 302.

Figure 9:
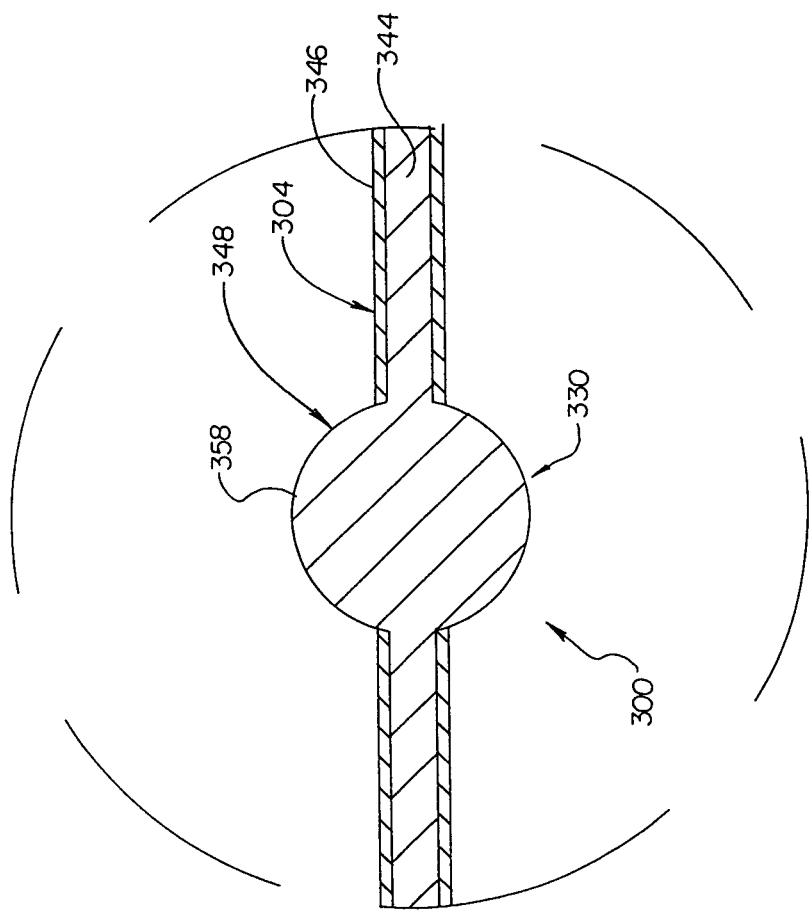
FIG. 9 is an enlarged cross-sectional view an electrode of the filter assembly of FIG. 5.

FIG. 9 is an enlarged cross-sectional view an electrode 348 of filter assembly 300 of FIG. 8. In FIG. 9 it may be appreciated that elongate shaft 304 of filter assembly 300 includes an insulating layer 346 and a electrically conductive core 344. In a preferred embodiment, insulating layer 346 overlays a substantial portion of electrically conductive core 344.

In FIG. 9, it may also be appreciated that each electrode 348 of filter assembly 300 comprises an electrode body 358 that is coupled to electrically conductive core 344 of elongate shaft 304. In a preferred embodiment, insulating layer 346 defines a plurality of openings 330. In the embodiment of FIG. 8 and FIG. 6, each opening 330 corresponds with an electrode body 358. Thus, it may be appreciated that insulating layer 346 does not substantially cover electrodes 348. Openings 330 defined by insulating layer 346 preferably allow direct contact between one or more electrode bodies 358 and debris that has been captured by filter 302. This contact preferably creates a conductive path between electrically conductive core 344 and the captured debris. In a preferred embodiment, electrodes 348 may be utilized to ablate debris that is disposed within filter 302.

Insulating layer 346 may comprise various materials without deviating from the spirit and scope of the present invention. Examples of materials which may be suitable in some applications include fluoropolytetrafluoroethylene (PTFE), polyethylene (PE), polypropylene (PP), polyvinylchloride (PVC), and polyurethane. A number of manufacturing processes may be used to create insulating layer 346. For example, a portion of insulating layer 346 may be made up of sections of shrink tubing. The shrink tubing sections may be positioned over electrically conductive core 344 of elongate shaft 304 then shrunk by the application of heat. A spray process may also be used to apply insulating layer 346 to filter 302. For example, PTFE solids in a suitable solvent carrier may be applied to electrically conductive core 344 using a spraying process.

Another material that may be used to fabricate insulating layer 346 is a thermoplastic generically known as parylene. There are a variety of polymers based on para-xylylene. These polymers are typically placed onto a substrate by vapor phase polymerization of the monomer. Parylene N coatings are produced by vaporization of a di(P-xylylene)dimer, pyrollization, and condensation of the vapor to produce a polymer that is maintained at comparatively lower temperature. In addition to parylene-N, parylene-C is derived from di(monochloro-P-xylylene) and parylene-D is derived from di(dichloro-P-xylylene). It is to be appreciated that parylene may be applied in various ways without deviating from the spirit and scope of the present invention.

FIG. 10 is an enlarged cross-sectional view an electrode 448 for use in a filter assembly 400 in accordance with an additional exemplary embodiment of the present invention. Electrode 448 may, for example, be used in the filter assembly of FIG. 9. Filter assembly 400 of FIG. 10 includes an elongate shaft 404 comprising an electrically conductive core 444 and an insulating layer 446. In a preferred embodiment, insulating layer 446 overlays a substantial portion of electrically conductive core 444. Electrode 448 of filter assembly 400 comprises an opening 430 defined by insulating layer 446. Opening 430 defined by insulating layer 446 preferably allows direct contact between electrically conductive core 444 and debris that has been captured by a filter of filter assembly 400. This contact preferably creates a conductive path between electrically conductive core 444 and the captured debris. In a preferred embodiment, electrode 448 may be utilized to ablate debris that is disposed within a filter of filter assembly 400.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A filter assembly for capturing debris within a blood vessel, comprising:
    an elongate shaft having a proximal end and a distal end;
    a filter disposed proximate the distal end of the elongate shaft, the filter including a filtering region and an attachment region, the filter having an expanded and a contracted shape;

in the expanded shape, the filtering region a major opening defined adjacent the filtering region proximal end and consisting of a single layer of filter membrane defining a filter basket and extending between the major opening and the distal end of the filtering region, the filter membrane having a plurality of apertures defined therein that are configured to allow the passage of blood through the filtering region;

the filter membrane further comprising a first generally linearly tapered portion and a second generally linearly tapered portion, the first generally linearly tapered portion defining a first included angle, and the second generally linearly tapered portion extending proximally from a proximal portion of the first tapered portion, the second generally linearly tapered portion defining a second included angle greater than the first included angle; and wherein the first generally linearly tapered portion extends at the first included angle for a length of the first generally linearly tapered portion and the second generally linearly tapered portion extends at the second included angle for a length of the second generally linearly tapered portion;

wherein the filter assembly further comprises an expandable frame disposed within and supporting the first generally linearly tapered portion and the second generally linearly tapered portion.

2. The filter assembly of claim 1, wherein the first tapered portion has a conical shape.

3. The filter assembly of claim 1, wherein the second tapered portion has a frustoconical shape.

4. The filter assembly of claim 1, wherein the filter membrane includes polyurethane.

5. The filter assembly of claim 1, wherein the expandable frame comprises a shape memory material.

6. The filter assembly of claim 5, wherein the shape memory material comprises a shape memory alloy.

7. The filter assembly of claim 6, wherein the shape memory alloy comprises Nitinol.

8. The assembly of claim 1, wherein the expandable frame includes a plurality of filter struts each having a proximal end and a distal end.

9. The assembly of claim 8, wherein said plurality of filter struts are adapted to bias the filter in an expanded position.

10. The assembly of claim 8, wherein the proximal end of each filter strut is connected to a filter mouth frame.

11. The assembly of claim 1, further including a retrieval sheath for retrieving the filter.

12. The filter assembly of claim 11, wherein the first tapered portion has a base diameter, the base diameter being smaller than an inner diameter of the retrieval sheath.

13. The assembly of claim 11, wherein the first tapered portion has a base diameter, the base diameter being similar to an inner diameter of the retrieval sheath.

14. The filter assembly of claim 11, wherein second tapered portion has a first diameter at the base diameter and a second diameter greater than the first diameter, and wherein the first diameter is similar to the inner diameter of the retrieval sheath when the filter assumes an expanded shape.

15. The filter assembly of claim 1, wherein the attachment region extends proximally from the filtering region, attaching a proximal end of the filtering region to the elongate shaft.

16. The filter assembly of claim 1, wherein the attachment region comprises struts that extend from the major opening in a generally proximal direction to attach to the elongate member.

17. A filter assembly for capturing debris within a blood vessel, comprising:
an elongate shaft having a proximal end and a distal end;
a filter disposed proximate the distal end of the elongate shaft, the filter having an expanded and a contracted shape, the filter including a filtering region and an attachment region, the filtering region defining a major opening adjacent a proximal end of the filtering region;
the attachment region comprising at least one strut extending proximally from adjacent the major opening to the elongate shaft;
in the expanded shape, the filtering region consisting of a single layer of filter membrane defining a filter basket and extending between the major opening and the distal end of the filtering region, the filter membrane having a plurality of apertures defined therein that are configured to allow the passage of blood through the filtering region;
the filtering region further comprising a first generally linearly tapered portion and a second generally linearly tapered portion, the first generally linearly tapered portion defining a first included angle and the second generally linearly tapered portion defining a second included angle which is different than the first included angle; and
wherein the first generally linearly tapered portion extends at the first included angle for a length of the first generally linearly tapered portion and the second generally linearly tapered portion extends at the second included angle for a length of the second generally linearly tapered portion;
wherein the filter assembly further comprises an expandable frame disposed within and supporting the first generally linearly tapered portion and the second generally linearly tapered portion.

18. The filter assembly of claim 17, wherein the first tapered portion has a conical shape.

19. The filter assembly of claim 17, wherein the second tapered portion has a frustoconical shape.

20. The filter assembly of claim 17, wherein the filter membrane includes polyurethane.

21. The filter assembly of claim 17, wherein the expandable frame comprises a shape memory material.

22. The filter assembly of claim 21, wherein the shape memory material comprises a shape memory alloy.

23. The filter assembly of claim 22, wherein the shape memory alloy comprises Nitinol.

24. The assembly of claim 17, wherein the expandable frame includes a plurality of filter struts each having a proximal end and a distal end.

25. The assembly of claim 24, wherein said plurality of filter struts are adapted to bias the filter in an expanded position.

26. The assembly of claim 24, wherein the proximal end of each filter strut is connected to a filter mouth frame.

27. The assembly of claim 17, further including a retrieval sheath for retrieving the filter.

28. The filter assembly of claim 27, wherein the first tapered portion has a base diameter, the base diameter being smaller than an inner diameter of the retrieval sheath.

29. The assembly of claim 27, wherein the first tapered portion has a base diameter, the base diameter being similar to an inner diameter of the retrieval sheath.

30. The filter assembly of claim 27, wherein second tapered portion has a first diameter at the base diameter and a second diameter greater than the first diameter, and wherein the first diameter is similar to the inner diameter of the retrieval sheath when the filter assumes an expanded shape.

31. The filter assembly of claim 17, wherein the second tapered portion extends proximally from a proximal portion of the first tapered portion.

32. The filter assembly of claim 17, wherein the single layer of filter membrane includes the first and second tapered portions.

33. The filter assembly of claim 17, wherein the second included angle is larger than the first included angle.

34. The filter assembly of claim 17, wherein the attachment region includes four struts.

* * * * *